US008349314B2

(12) United States Patent
Stanford et al.

(10) Patent No.: US 8,349,314 B2
(45) Date of Patent: Jan. 8, 2013

(54) METHOD OF TREATING AND/OR PREVENTING TYPE II DIABETES USING ACTINOMYCETALES

(75) Inventors: John Lawson Stanford, Nr Tonbridge (GB); Cynthia Ann Stanford, Nr Tonbridge (GB); Graham McIntyre, West Wickham (GB); Oscar Adelmo Bottasso, Coronel Bogado (AR)

(73) Assignee: BIOEOS Limited, Woodmansterne, Surrey (GB)

( * ) Notice: Subject to any disclaimer, the term of this patent is extended or adjusted under 35 U.S.C. 154(b) by 1131 days.

(21) Appl. No.: 12/198,496

(22) Filed: Aug. 26, 2008

(65) Prior Publication Data

US 2009/0060877 A1 Mar. 5, 2009

(30) Foreign Application Priority Data

Aug. 29, 2007 (GB) .................................. 0716778.6

(51) Int. Cl.
*C12N 1/00* (2006.01)
(52) U.S. Cl. ...................................................... 424/93.4
(58) Field of Classification Search .......................... None
See application file for complete search history.

(56) References Cited

U.S. PATENT DOCUMENTS

| 8,101,166 B2 * | 1/2012 | Solinger et al. ............. 424/85.2 |
| 2003/0143701 A1 | 7/2003 | Matsuyama et al. |
| 2007/0135504 A1 * | 6/2007 | Marshall ....................... 514/381 |

FOREIGN PATENT DOCUMENTS

| EP | 0654534 A2 | 11/1994 |
| WO | WO 96/12794 | 5/1996 |
| WO | WO 96/29425 | 9/1996 |
| WO | WO 02/32455 A2 | 4/2002 |
| WO | WO 2004/022093 A1 | 3/2004 |
| WO | WO 2005/049056 A2 | 6/2005 |
| WO | WO 2007/071978 | * 6/2007 |
| WO | WO 2007/071982 | * 6/2007 |

OTHER PUBLICATIONS

Calderari, Susana, et al., Rat News Letter (1991) vol. 25 pp. 28-29.
Diez, Marianne, "The Royal Canin cut-out and keep guide to body condition scoring in cats and dogs," *Waltham Focus* (2006) vol. 16:1 pp. 39-40.
Suzuki, Kunio, et al., "A fermentation product of phytosterol including campestenone reduces body fat storage and body weight gain in mice," *J. Nutr. Sci. Vitaminol.* (2007) vol. 53:1 pp. 63-67.
Alberti, K.G.M.M., et al., "Definition, diagnosis and classification of diabetes mellitus and its complications, Part 1: Diagnosis and classification of diabetes mellitus provisional report of a WHO consultation," Diabet Med. (1998) vol. 15 pp. 539-553.
Bergey's Manual of Determinative Bacteriology, inth Edition Group 22 (1994).
Bohan, Michelle, "Plane of Nutrition Affects Plasma Gherlin Concentrations in Neonatal Calves," *Iowa State University Animal Industry Report 2007 A.S. Leaflet R2199* (2007).
Choi, Beom-Kyu, et al., "Prevention of encephalomyocarditis virus-induced diabetes by live recimbinant *Mycobacterium bovis* bacillus calmette-guerin in susceptible mice," *Diabetes* (2000) vol. 49 pp. 1459-1467.
Gianani, Roberto, et al., "The stages of type 1A diabetes: 2005" *Immunological Reviews* (2005) vol. 204 pp. 232-249.
Hotamisligil, Gokhan, S., et al., Tumor necrosis factor α inhibits signal Proc. Natl. Acad. Sci. USA (1994) vol. 91 pp. 4854-4858.
Kolb, H., et al., "An immune origin of type 2 diabetes?," *Diabetologia* (2005) vol. 48 pp. 1038-1050.
Martines, Stella M., et al., "Spontaneous Diabetes in eSS Rats," *Medicina* (1984) vol. 44 pp. 145-152.
Martinez, Stella Maris, et al., "eSS rat, an animal model for the study of spontaneous non-insulin-dependent diabetes," *Lessons from animal diabetes IV* (1993) E. Shafrir, Smith-Gordon, Chapter 8 pp. 75-90.
Martinez, Stella Maris, et al., "Modelo murino de la diabetes clinicamente benigna de los jovenes (MODY)," Medicina (1984) vol. 44 pp. 145-152.
Martins, T.C., et al., "Mechanisms of *Mycobacterium avium*-induced resistance against insulin-dependent diabetes mellitus (IDDM) in non-obese diabetic (NOD) mice: role of Fas and Th1 cells," *Clin. Exp. Immunol.* (1999) vol. 115 pp. 248-254.
Matsuzaki, Taeshi, et al. "Antidiabetic effects of an oral administration of lactobacillus case in a non-insulin-dependenr diabetes mellitus (NIDDM) model using KK-A$^y$ Mice," *Endocrine Journal* (1997) vol. 44:3 pp. 357-365.
Nomaguchi, Hiroko, et al., "Prevention of diabetes in non-obese diabetic mice by a single immunization with *Mycobacterium leprea*," *Japanese Journal Leprosy* (2002) vol. 17 pp. 31-38.
Pasarica, H., et al. "Human adenovirus 36 induces adiposity, increases insulin sensitivity, and alters hypothalamic monoamines in rates," *Obesity* (2006) vol. 14:11 pp. 1905-1913.
Shahabi, Shahram,et al., "Sympathetic nervous system plays an important role in the relationship between immune mediated diseases," Medical Hypotheses (2006) vol. 67:4 pp. 900-903. Stosic-Grujicic, et al., "Preventation of experimental autoimmune diabetes in mice by treatment with mycobacteria and their components," *Mikrobiolgija* (1996) vol. 33:1 pp. 27-36 XP001095359.
Tarres, Maria, Cristina, et al., "The eSS rat," *American Journal of Pathology* (1992) vol. 141:3 pp. 761-763.
Tarrest, M.C., et al., "The eSMT rat: a murine model of type 2 diabetes," *Proceeding on the International Joint Meeting Twelfth General Assembly and Conference and Seventh FELASA Symposium* (May 1999) pp. 93-94.
Vangipuram, S.D., et al., "Adipogenic human adenovirus-36 reduces leptin expression and secretion and increases glucose uptake by fat cells," *International Journal of Obesity* (2007) vol. 31 pp. 87-96.

(Continued)

*Primary Examiner* — Allison Ford
(74) *Attorney, Agent, or Firm* — Steptoe & Johnson LLP

(57) ABSTRACT

Use of whole cells of bacteria from the genera of aerobic organisms in the order of Actinomycetales in the manufacture of a medicament for the treatment or prevention of Type II diabetes and/or obesity and methods of treating or preventing Type II diabetes and/or obesity in a subject by administering an effective amount of a composition comprising a whole cell of a bacterium from a genera of aerobic organisms in the order of Actinomycetales to said subject. Preferably the bacteria is from one or more of the following genera for example: *Gordonia, Rhodococcus, Tsukamurella, Nocardia, Dietzia* and *Mycobacterium*.

11 Claims, 2 Drawing Sheets

OTHER PUBLICATIONS

Figure 1:
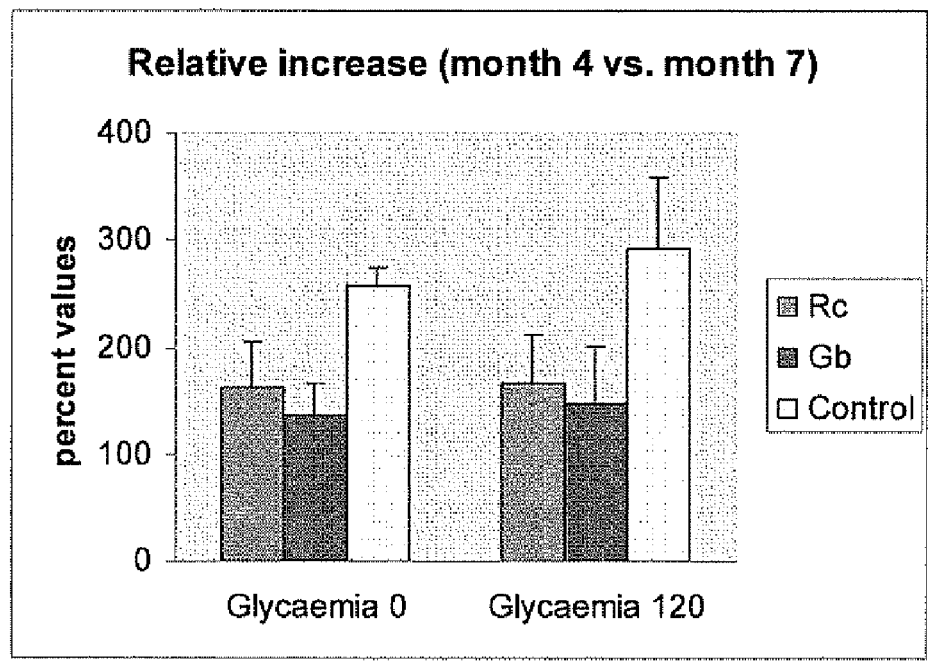

Vasilakopoulou, A., et al., "Could a virus contribute to weight gain?," *International Journal of Obesity* (2007) vol. 13 pp. 1350-1356.

Wikipedia entry for Diabetes mellitus type 2, May 11, 2007 (http://en.wikipedia.org/wiki/Type_2_diabetes).

Martinez et al, Spontaneous Diabetes in eSS Rats, Acta Diabetol Lat, 1988, vol. 25, p. 303-313.

Olguín et al., Diabetes, Nutrition & Metabolism Clinical and Experimental, 1998, vol. 1, p. 314-319.

Remington's Pharmaceutical Sciences, Gennaro (ed), Mack Publishing Co., 1985.

Goodfellow, M., et al., *Rhodococcal systematics: problems and developments*, Antonie van Leeuwenhock, 74: 3-20 (1998).

\* cited by examiner

METHOD OF TREATING AND/OR PREVENTING TYPE II DIABETES USING ACTINOMYCETALES

CLAIM OF PRIORITY

This application claims priority under 35 USC 119 to British Patent Application No. 0716778.6, filed on Aug. 29, 2007, which is incorporated by reference in its entirety.

FIELD OF INVENTION

The present invention relates to the use of a composition and/or pharmaceutical composition for the treatment and/or prevention of Type II diabetes, methods of treating a subject with a composition and/or pharmaceutical composition in order to treat and/or prevent Type II diabetes, and a pharmaceutical pack comprising a composition and/or pharmaceutical composition.

BACKGROUND TO THE INVENTION

Type II diabetes (non-insulin dependent diabetes) is a common metabolic disorder that is rapidly increasing particularly in the developed world. It can be characterised by insulin resistance, insulin deficiency and hyperglycaemia. Factors that are linked with Type II diabetes include elevated cholesterol, obesity and hypertension.

Type II diabetes may not be diagnosed for many years since symptoms may be sporadic and are certainly milder than those associated with Type I diabetes. However, elevated blood sugar levels in untreated Type II diabetes sufferers can lead to functional impairment of kidneys, eyes and cardiovascular systems.

Whole cells of *Mycobacterium* (such as *Mycobacterium avium*, *Mycobacterium leprae* and *Mycobacterium bovis*) have been taught to play a role in the treatment of Type I diabetes. However, such bacteria have not been implicated in the prevention and/or treatment of Type II diabetes.

For the avoidance of doubt, Type 1 Insulin-dependent diabetes mellitus (IDDM or T1 Diabetes) and Type II diabetes differ in origin.

Type I may be characterized by an immune attack of the insulin-producing cells in the pancreatic islets. Studies in the NOD mouse, an inbred strain derived in Japan, showed that a high proportion of NOD mice spontaneously develop Type 1 diabetes due to destruction of pancreatic islets that is mediated by autoreactive T cells and closely resembles the human disease.

Occurrence of an autoimmune disease may primarily reflect the weakness of tolerogenic responses to these self-antigens rather than an enhancement of immunogenic stimuli. In addition to tolerance mediated by cell-intrinsic responses of deletion and anergy, it has long been speculated that tolerance might be mediated by regulatory/suppressor cells that are induced by stimulation with self-antigens in the thymus.

In contradistinction, Type 2 diabetes may be caused by the failure of beta cells to compensate for insulin resistance. High-caloric diets and insufficient muscle work seem to be important environmental factors involved in the pathogenesis of obesity and Type 2 diabetes. Environmental factors seem to act via two major targets. One is the processing of glucose, fatty acids and other metabolites, as regulated by insulin and other hormones in the majority of tissues, and the other is beta cell function.

Obesity has become a major public health problem. Health conditions caused or exacerbated by obesity include hypertension, diabetes mellitus, sleep apnea, obesity-related hypoventilation, back and joint problems, cardiovascular disease, non-alcoholic fatty liver disease and gastroesophageal reflux disease.

The body mass index (BMI) (calculated as weight in kilograms divided by the square of height in meters) is the most commonly accepted measurement for overweight and/or obesity. A BMI exceeding 25 is considered overweight, while obesity is defined as a BMI of 30 or more, with a BMI of 35 or more considered as serious comorbidity and a BMI of 40 or more considered morbid obesity.

SUMMARY OF THE INVENTION

A seminal finding of the present invention is that Type-II diabetes can be treated and/or prevented and/or reduced by administration of a whole cell of a bacterium from a genus of aerobic organisms in the order Actinomycetales, in particular, by administration of a whole cell of a bacterium from an aerobic Actinomycete.

Another seminal finding of the present invention is that obesity can be treated and/or prevented and/or reduced by administration of a whole cell of a bacterium from a genus of aerobic organisms in the order Actinomycetales, in particular, by administration of a whole cell of a bacterium from an aerobic Actinomycete.

DETAILED ASPECTS OF THE INVENTION

In one aspect, the present invention provides the use of a composition comprising whole cells of bacteria from a genus of aerobic organisms in the order Actinomycetales in the manufacture of a medicament for the treatment or prevention of Type II diabetes and/or obesity, preferably Type II diabetes.

In a further aspect, the present invention provides a method for treating or preventing Type II diabetes and/or obesity in a subject comprising administering an effective amount of a composition, preferably a pharmaceutical composition, comprising a whole cell of bacteria from a genus of aerobic organisms in the order Actinomycetales, to a subject.

Suitably, the effective amount of the composition, preferably the pharmaceutical composition, may be administered as a single dose. Alternatively, the effective amount of the composition, preferably the pharmaceutical composition, may be administered in multiple (repeat) doses, for example two or more, three or more, four or more, five or more, six or more, ten or more, twenty or more repeat doses.

In another aspect, the present invention provides a method for protecting, including immunising, a subject from Type II diabetes and/or obesity comprising administering a composition, preferably a pharmaceutical composition, comprising whole cells of bacteria from a genus of aerobic organisms in the order Actinomycetales, to the subject.

In a further aspect, the present invention provides a pharmaceutical pack for use in the treatment of Type II diabetes and/or obesity wherein at least one compartment comprises whole cells of bacteria from a genus of aerobic organisms in the order Actinomycetales.

Type II diabetes can be characterised by insulin resistance, insulin deficiency and/or hyperglycaemia. The term "condition associated therewith" as used herein means a condition which characterises Type II diabetes, such as insulin resistance, insulin deficiency, hyperglycaemia and metabolic syndrome.

In a further aspect of the present invention there is provided use of a composition comprising whole cells of bacteria from a genus of aerobic organisms in the order of Actinomycetales in the manufacture of a medicament for the treatment or prevention of one or more of insulin resistance when associated with Type II diabetes, insulin deficiency when associated with Type II diabetes, hyperglycaemia when associated with Type II diabetes and metabolic syndrome when associated with Type II diabetes.

The term "metabolic syndrome" as used herein may be defined as glucose intolerance, or diabetes and/or insulin resistance, together with two or more of the following risk factors: impaired glucose regulation or diabetes; insulin resistance; increased arterial pressure $\geqq 160/90$ mm Hg; increased plasma triglycerides ($\geqq 1.7$ mmol/L) and/or low HDL cholesterol (<0.9 mmol/L men, <1.0 mmol/L women); central obesity (waist-to-hip ratio$\geqq 0.9$ men, $\geqq 0.85$ women) and/or Body Mass Index (BMI)$\geqq 30$; and microalbuminuria (*Diabet Med*, 1998; 15:539-553).

In a yet further aspect of the present invention there is provided a method for treating or preventing preferably treating) one or more of insulin resistance when associated with Type II diabetes, insulin deficiency when associated with Type II diabetes, hyperglycaemia when associated with Type II diabetes and metabolic syndrome when associated with Type II diabetes in a subject comprising administering an effective amount of a composition comprising whole cells of bacteria from a genus of aerobic organisms in the order of Actinomycetales, to said subject.

Suitably, in addition and/or in the alternative to the uses and methods described above, the use of the composition comprising whole cells of bacteria from a genus of aerobic organisms in the order of Actinomycetales may treat or prevent a reduction in the size, preferably mean size, of Langerhans islets associated with Type II diabetes.

In one aspect, the present invention provides the use of a composition comprising whole cells of bacteria from a genus of aerobic organisms in the order Actinomycetales in the manufacture of a medicament for the treatment or prevention of a reduction in the size, preferably mean size, of Langerhans islets.

In a further aspect, the present invention provides a method for treating or preventing the reduction or prevention in the size, preferably mean size, of Langerhans islets in a subject comprising administering an effective amount of a composition comprising whole cells of bacteria from a genus of aerobic organisms in the order of Actinomycetales, to said subject.

By the term "reduction in the size of Langerhans islets" we mean a reduction in the size, preferably mean size, of Langerhans islets compared with the size, preferably mean size, of Langerhans islets in a healthy individual. Typically the reduction in the size of Langerhans islets will have been caused by an individual having diabetes, such as Type II diabetes.

Therefore in other words in addition and/or in the alternative to the uses and methods described above, the use of the composition comprising whole cells of bacteria from a genus of aerobic organisms in the order of Actinomycetales may increase the size, preferably mean size, of Langerhans islets in individuals with Type II diabetes. Suitably the Langerhans islets are increased to the size normally associated with a healthy individual.

A Langerhans islet with a diameter oscillating between the diameter of 1 to less than 3 pancreatic acini's may be defined as small; whereas an islet showing a diameter equal or greater than 3 pancreatic acini's may be regarded as large.

Preferably in individuals treated with the composition comprising whole cells of bacteria from a genus of aerobic organisms in the order of Actinomycetales the proportion of large islets to small islets is increased. This increase is compared with the proportion in an untreated control individual.

As used herein the term "Type II diabetes" refers to non-insulin dependent diabetes mellitus.

The term "whole cells of bacteria from a genus of aerobic organisms in the order of Actinomycetales" as used herein encompasses whole cells of one or more strains of bacteria. Suitably, where the whole cells are from more than one strain of bacteria, said strains may be from one or more species within the same genus and/or one or more genera. Suitably, where said whole cells are from more than one genera, said genera may be from one or more families. Thus, by way of example only the term may encompass whole cells from one particular bacterial strain (for example, whole cells of a particular strain of *Gordonia bronchialis*) and/or whole cells of bacteria from more than one species and/or genera of aerobic organisms, such as by way of example only, whole cells of bacteria from the species *Gordonia bronchialis* and *Rhodococcus coprophilus*.

Whole cells of bacteria from the aerobic actinomycete genera can have a corrective influence on immunologically mediated damage.

In another embodiment, suitably the aerobic organism(s) in the order Actinomycetales for use in accordance with the present invention may be Nocardioform actinomycetes (such as bacteria mentioned in Group 22 of Bergy's Manual of Determinative Bacteriology, Ninth Edition; such as, for example, mycolic-acid containing bacteria).

Preferably, the aerobic organism(s) are mycolic acid-containing bacteria (such as bacteria in Group 22 subgroup 1 of Bergy's Manual of Determinative Bacteriology, Ninth Edition; such as, for example, *Tsukamurella, Rhodococcus, Norcardia* and *Gordonia*).

Without wishing to be bound by theory, it is believed that unusual cell wall lipid(s) present in such bacteria may play a role in the treatment and/or prevention of Type II diabetes, obesity and/or a condition associated therewith.

Preferably, the bacteria may be from one or more of the following genera: *Gordonia* (such as *C. bronchialis, G. amarae, G. sputi* and *G. terrae*, preferably *G. bronchialis*); *Rhodococcus* (such as *Rhodococcus ruber* (previously known as *Nocardia rubra*), *R. rhodnii, R. coprophilus, R. opacus* and *R. erythopolis*, preferably from *R. coprophilus*); *Tsukamurella* (such as *T. inchonensis* and *T. paurometabola*, preferably from *T. inchonensis*); and *Norcardia* (such as *Norcardia asteroides* and *N. brasiliensis*).

In yet another embodiment, suitably the bacteria in the order Actinomycetales for use in accordance with the present invention may be from a genus or genera that contain mycolic acid as a component of the cell wall. Examples of such genera include: *Tsukamurella, Mycobacterium, Dietzia, Rhodococcus, Norcardia* and *Gordonia*.

Preferably, the bacteria in the order Actinomycetales for use in accordance with the present invention is/are from one or more of the following genera: *Gordonia* (such as *G. bronchialis, G. amarae, G. sputi* and *G. terrae*, preferably *G. bronchialis*); *Rhodococcus* (such as from *Rhodococcus ruber* (previously known as *Nocardia rubra*), *R. rhodnii, R. coprophilus, R. opacus* and *R. erythopolis*, preferably from *R. coprophilus*); *Tsukarmurella* (such as *T. inchonensis* and *T. paurometabola*, preferably from *T. inchonensis*); Mycobacterium (such as from *M. vaccae* and *M. obuense*, preferably from *M. obuense*); *Dietzia* (such as *Dietzia maris*) and *Norcardia* (such as from *Norcardia asteroides* and *N. brasiliensis*).

Suitably the bacteria may be from the genus *Gordonia*. Preferably, the bacteria are one or more of the following: *G. bronchialis, G. amarae, G. sputi* and *G. terrae*, more preferably *G. bronchialis*.

The genus *Gordonia* used herein may also be referred to as Gordona. It is intended herein that these terms are interchangeable.

Suitably the bacteria may be selected from the genus *Rhodococcus*. Suitably, the bacteria may be selected from any one or more of the following species: *Rhodococcus ruber* (previously known as *Nocardia rubra*), *R. rhodnii, R. coprophilus, R. opacus* and *R. erythopolis*, more preferably from *R. coprophilus*.

Suitably the bacteria may be from the genus *Tsukamurella*. Preferably, the bacteria are *T. inchonensis* and/or *T. paurometabola*; more preferably *T. inchonensis*.

Suitably the bacteria may be from the genus *Mycobacterium*. Suitably, the bacteria may be *M. vaccae* and/or *M. obuense*, preferably *M. obuense*.

A *M. obuense* strain for use in accordance with the present invention has been deposited by BioEos Limited of 67 Lakers Rise, Woodmansterne, Surrey, SM7 3LA under the Budapest Treaty on the International Recognition of the Deposit of Microorganisms for the purposes of Patent Procedure at the National Collection of Type Cultures (NCTC), Central Public Health Laboratory, 61 Colindale Avenue, London, NW9 5HT) on the 14 Jul. 2005, under Accession Number NCTC 13365. Suitably the bacteria may be from the genus *Dietzia*. Suitably, the bacteria may be *Dietzia maris*.

Suitably the bacteria may be selected from the genus *Norcardia*. Suitably, the bacteria may be selected from any one or more of the following species: *Norcardia asteroides* and/or *N. brasiliensis*.

Preferably the bacteria for use in the present invention are killed prior to use. Hence in a preferred embodiment the use of killed whole cell bacteria is preferred.

In a preferable embodiment a pharmaceutical pack according to the present invention further comprises a label stating that it is suitable for use in the prevention or treatment of Type II diabetes and/or obesity.

In one embodiment the pharmaceutical pack in accordance with the present invention may comprise a label stating that it is suitable for use in the prevention or treatment of one or more of insulin resistance when associated with Type II diabetes, insulin deficiency when associated with Type II diabetes, hyperglycaemia when associated with Type II diabetes and metabolic syndrome when associated with Type II diabetes.

The composition may be administered to the subject as a single dose or in multiple doses. In one embodiment, preferably the composition may be administered to the subject in multiple doses.

The composition may be administered in more than one dose. The doses may be delivered sequentially and even by different administration routes.

In one embodiment, initially the composition may be administered in at least two doses. By way of Example only, the composition may be administered weekly, every two weeks, every three weeks, every month, every six weeks, every two months, every three months or every four months. The composition may be administered at least once every four weeks.

In one embodiment, the composition may be administered throughout the lifetime of the subject. Suitably, the subject may receive up to three or four doses per year (i.e. the subject may be administered every three or four months, for example).

In a particular embodiment, the composition may initially be administered to a subject at regular intervals (such as weekly or monthly intervals) and later administrations may be at intervals of three or four months. For example, a subject may receive three doses at monthly intervals (or perhaps 6 doses at two week intervals) and subsequent doses at three monthly intervals.

Preferably each dose is administered as an injection.

The term "treatment" and/or "treating" as used herein may include "controlling" the Type II diabetes, obesity and/or a condition associated therewith, preferably Type II diabetes and/or obesity. For instance the term "treatment" and/or "treating" as used herein may be palliative or prophylactic. In other words when administered the composition, a subject may not be completely treated of the Type II diabetes and/or a condition associated therewith, but the Type II diabetes and/or a condition associated therewith may be in remission.

In some embodiments the term "treatment" and/or "treating" means that the Type II diabetes and/or a condition associated therewith, preferably Type II diabetes is controlled.

The term "preventing" and/or "prevention" as used herein means that the subject is less susceptible to the Type II diabetes and/or a disease and/or disorder associated therewith as compared with a subject not administered with the compositions according to the present invention and/or that the subject is more able to counter or overcome the Type II diabetes and/or a disease and/or disorder associated therewith as compared with a subject not administered with the compositions according to the present invention.

The term "whole cell", as used herein, means a bacterium which is intact, or substantially intact. In particular, the term "intact" as used herein means a bacterium which is comprised of all of the components present in a whole cell, particularly a whole, viable cell, and/or a bacterium which has not been specifically treated to remove one or more components from it. By the term "substantially intact" as used herein it is meant that although the isolation and/or purification process used in obtaining the bacterium may result in, for example, a slight modification to the cell and/or in the removal of one or more of the components of the cell, the degree to which such a modification and/or removal occurs is insignificant. In particular, a substantially intact cell according to the present invention has not been specifically treated to remove one or more components from it.

For the avoidance of doubt in the preferred embodiment the bacterium is not a ground bacterium or has not undergone grinding prior to administration.

For the avoidance of doubt, when it is the case that the bacterium is killed prior to use, for example by heat-treatment, such heat treatment may inactivate or destroy constituents of the bacterium. Such a killed, for example heat treated, bacterium may still be considered as a substantially intact whole cell in accordance with the present invention.

WO2004/022093 and WO2005/049056 (both of which references are incorporated herein by reference) disclose a composition (e.g. a pharmaceutical composition) comprising a whole cell of a bacterium from the genera *Rhodococcus, Gordonia, Nocardia, Dietzia, Tsukamurella* and *Nocardioides*. However, neither of these documents teaches or suggests the use of such an immune modulator composition or pharmaceutical composition for the treatment and/or prevention of Type II diabetes.

*Mycobacterium vaccae*, or part thereof (as taught in WO2002/032455), has been used in a vaccine against mycobacterial disease (e.g. tuberculosis). However the use of *M. vaccae* in the prevention or treatment of Type II diabetes has not been previously taught nor suggested.

Suitably, the composition or pharmaceutical composition used herein may comprise a pharmaceutically acceptable carrier, diluent or excipient.

Suitably, the composition and/or pharmaceutical composition may comprise more than one whole cell, and more preferably comprises a plurality of whole cells.

In one aspect, the composition and/or a pharmaceutical composition comprising a whole cell of a bacterium from a genus of aerobic organisms in the order Actinomycetales may further comprise at least one, or at least one further, antigen or antigenic determinant.

Suitably, the composition for use in accordance with the present invention may comprise two or more, or three or more, bacteria from a genus of aerobic organisms in the order Actinomycetales.

Preferably, the bacteria for use in accordance with the present invention are species which can be grown on a medium, which is a low, preferably non-antigenic medium. By way of example only, a suitable non-antigenic medium is Sauton's medium.

The term "subject", as used herein, means a human and/or animal. Preferably, the subject is a mammal, including for example domesticated animals (such as cats and dogs) and/or humans. However, should Type II diabetes and/or obesity be identified in another subject, such as a different animal, it is envisaged that the composition and/or pharmaceutical composition taught herein would be effective to treat and/or prevent Type II diabetes and/or obesity in other subjects, such as in other animals. In one embodiment preferably the subject is a human. Preferably, the subject is an adult.

Preferably, the subject has Type II diabetes or a predisposition for Type II diabetes. The term "predisposition to Type II diabetes" as used herein refers to a subject with an increased likelihood of developing Type II diabetes compared with a healthy subject. For instance, subjects with a predisposition to Type II diabetes in accordance with the present invention include those which have one or more of the following: high cholesterol, hypertension, obesity or a genetic disposition.

Preferably, the composition of the present invention is used in the treatment of Type II diabetes by administering the composition to a subject with diabetes.

Suitably, the composition of the present invention may be used in the treatment of obesity by administering the composition to a subject with obesity.

In some embodiments of the present invention the subject may be an overweight subject (for example have a BMI of greater than 25, preferably greater than 30) and/or be at risk of becoming obese (e.g. due to the subject's diet or for medical reasons such as metabolic reasons or side effects of medication).

Suitably, compositions of the present invention may prevent a subject becoming obese. By "prevent" it is meant that the compositions of the present invention may either keep a subject from becoming obese or delay the onset of obesity (i.e. slow down the rate at which the subject becomes obese) compared with the subject had they not been administered the composition of the present invention.

In addition or in the alternative, the subject may have a viral infection (such as a viral infection associated with weight gain).

Preferably, the bacterium according to the present invention is killed prior to use.

Preferably, the bacterium according to the present invention is killed by heat-treatment thereof, for example, heat-treatment in an autoclave at 121° C. for 15 minutes.

Other suitable treatments for killing the bacterium may include ultraviolet or ionising radiation or treatment with chemicals such as phenol, alcohol or formalin. Suitably the ionising radiation may be carried out by exposure to 2.5 Mrads from a $Co_{60}$ Source.

Preferably, the bacterium according to the present invention is purified and/or isolated.

Preferably, the bacterium according to the present invention is suspended in an aqueous solution (such as water or buffered saline, suitably borate buffered at pH 8). Preferably, the bacterium is not administered in an oil.

Suitably, the composition of the present invention may be a "therapeutic" composition which is administered to individuals with an existing condition to reduce or minimise the condition or to abrogate the immunopathological consequences of the condition.

Overweight/Obesity

For humans, the body mass index (BMI) (calculated as weight in kilograms divided by the square of height in meters) is the most commonly accepted measurement for overweight and/or obesity.

A BMI exceeding 25 is considered overweight.

Obesity is defined as a BMI of 30 or more, with a BMI of 35 or more considered as serious comorbidity and a BMI of 40 or more considered morbid obesity.

The term "obesity" as used herein includes obesity, comorbidity obesity and morbid obesity. Therefore, the term "obesity" as used here may be defined as a subject having a BMI of more than or equal to 30.

In some embodiments, suitably an obese subject may have a BMI of more than or equal to 30, suitably 35, suitably 40.

The term "excess weight" as used herein means the excess weight of the subject. The term "excess weight" as used herein means that that the subject is considered overweight. There term "overweight" as used herein means that the subject has a BMI exceeding 25.

Excess weight and/or obesity may be measured using the BMI. Therefore a reduction in excess weight and/or obesity may be measured using the BMI.

In one embodiment, in the treatment of obesity the BMI of the subject may be reduced by 5 units (i.e. from 35 to 30 BMI units; or from 30 to 25 BMI units), preferably by 10 units.

Suitably in the treatment of obesity the BMI of the subject may be reduced to less than 28, preferably less than 25, more preferably less than 20.

A reduction in excess weight and/or obesity may also (or alternatively) be measured simply by measuring the weight of the subject relative to a control and/or before and after administration of the microorganisms and/or metabolite thereof according to the present invention.

Without wishing to be bound by theory, there may also be a link between serum or blood inflammatory markers (such as C-reactive protein and/or interleukin 6 and/or TNF-RII for example) and obesity. In addition, there may also be a correlation between serum or blood inflammatory markers and BMI. Hence, in one embodiment one may measure blood inflammatory markers to determine obesity and/or a reduction in obesity in a subject.

Likewise, methods of determining whether animals (e.g. domesticated animals such as cats and dogs) are overweight and/or obese are well known. For instance, body conditioning scoring in cats and dogs may be used in which the evaluation is conducted in accordance with simple criteria such as the size and location of major adipose deposits, the visible and invisible skeletal structure and/or the silhouette of the animal (see Diez, The Royal Canin cut-out and keep guide to body condition scoring in cats and dogs, 2006, Volume 16, No. 1).

Disorders/Diseases Related to or Caused by Excess Weight and/or Obesity

Health conditions (i.e. disorders and/or diseases) caused or exacerbated by obesity include hypertension, diabetes mellitus, for example type-2 diabetes, sleep apnea, obesity-related hypoventilation, back and joint problems, cardiovascular disease, non-alcoholic fatty liver disease and gastroesophageal reflux disease.

Suitable compositions of the present invention may alleviate and/or ameliorate conditions related to or caused by obesity.

Administration

Typically, a physician will determine the actual dosage of the composition or pharmaceutical composition which will be most suitable for an individual subject and it will vary with the age, weight and response of the particular subject. The dosages below are exemplary of the average case. There can, of course, be individual instances where higher or lower dosage ranges are merited.

Preferably, the actual dosage that is used results in minimal toxicity to the subject.

The compositions of the present invention may be administered by direct injection. The composition may be formulated for parenteral, mucosal, intramuscular, intravenous, subcutaneous, intraocular, intradermal or transdermal administration.

Suitably, the composition according to the present invention may be administered at a dose of $10^3$-$10^{11}$ organisms, preferably $10^4$-$10^{10}$ organisms, more preferably $10^4$-$10^9$, more preferably $10^6$-$5\times10^9$ organisms, and even more preferably $10^7$-$2\times10^9$ organisms. Typically, the composition according to the present invention may be administered at a dose of $10^8$-$2\times10^9$ bacteria for human and animal use. Suitably these dosages are considered an "effective amount" in accordance with the present invention.

Preferably the composition may be administered at a dose of $10^4$-$10^{10}$ organisms. Suitably these dosages are considered an "effective amount" in accordance with the present invention.

As will be readily appreciated by a skilled person the dosage administered will be dependent upon the organism to which the dose is being administered. For example, in humans a typical dose may be up to and/or in the region of 1 mg/0.1 ml.

The term "administering" as used herein refers to administration of bacteria of the present invention for the purposes of providing a medicament. Preferably, "administering" relates to administration for the purpose of preventing, treating and/or controlling Type II diabetes and/or symptoms thereof (e.g. elevated blood sugar levels). In other words, in one embodiment the term "administering" means that the bacteria is given (preferably as a medicament) to the subject, i.e. does not encompass the situation where the subject may comprise or acquire the bacteria naturally.

The term "administered" includes delivery by delivery mechanisms including injection, lipid mediated transfection, liposomes, immunoliposomes, lipofectin, catonic facial amphiphiles (CFAs) and combinations thereof, or even viral delivery. The routes for such delivery mechanisms include but are not limited to mucosal, nasal, oral, parenteral, gastrointestinal, topical, or sublingual routes.

The term "administered" includes but is not limited to delivery by a mucosal route, for example, as a nasal spray or aerosol for inhalation or as an ingestible solution; a parenteral route where delivery is by an injectable form, such as, for example, an intravenous, intramuscular, intradermal or subcutaneous route.

The term "co-administered" means that the site and time of administration of each of the compositions, adjuvants(s), antigen(s) and/or antigenic determinant(s) of the present invention are such that the necessary modulation of the immune system is achieved. Thus, whilst the composition and either an antigen(s) and/or adjuvant(s) may be administered at the same moment in time and at the same site, there may be advantages in administering the composition and/or antigen(s) and/or antigenic determinant(s) at a different time and to a different site from the adjuvant(s). The composition and/or antigen(s) and/or antigenic determinant(s) and adjuvant(s) may even be delivered in the same delivery vehicle—and the antigen(s) and/or antigenic determinant(s) and adjuvant(s) may be coupled and/or uncoupled and/or genetically coupled and/or uncoupled. By way of example only, the composition according to the present invention may be administered before, at the same time or post administration of one or more antigens or further antigens.

The composition may be administered to the subject as a single dose or in multiple doses. Preferably the composition is administered in multiple doses.

The composition and/or pharmaceutical composition for use in accordance with the invention may be administered by a number of different routes such as injection (which includes parenteral, subcutaneous, intradermal and intramuscular injection) intranasal, mucosal, oral, intra-vaginal, urethral or ocular administration.

Preferably, in the present invention, administration is by injection. More preferably the injection is intradermal, subcutaneous and/or intravenous, preferably intradermal or subcutaneous.

Preferably, in the present invention, administration is by an orally acceptable composition.

For administration the composition may be provided in an aqueous solution, for example in 0.1 to 0.2 ml of an aqueous solution, preferably buffered physiological saline. Suitably the composition may be administered parenterally, for example by intradermal inoculation. The composition according to the invention is preferably injected intradermally. Slight swelling and redness, sometimes also itching may be found at the injection site. The mode of administration, the dose and the number of administrations can be optimised by those skilled in the art in a known manner.

Antigens

As used herein, an "antigen" means an entity which, when introduced into an immunocompetent host, modifies the production of a specific antibody or antibodies that can combine with the entity, and/or modifies the relevant T-helper cell response, such as Th2 and/or Th1. The antigen may be a pure substance, a mixture of substances or soluble or particulate material (including cells or cell fragments or cell sonicate). In this sense, the term includes any suitable antigenic determinant, cross reacting antigen, alloantigen, xenoantigen, tolerogen, allergen, hapten, and immunogen, or parts thereof, as well as any combination thereof, and these terms are used interchangeably throughout the text.

The term "antigenic determinant or epitope" as used herein refers to a site on an antigen which is recognised by an antibody or T-cell receptor, or is responsible for evoking the T-helper cell response. Preferably it is a short peptide derived from or as part of a protein antigen. However the term is also intended to include glycopeptides and carbohydrate epitopes. The term also includes modified sequences of amino acids or carbohydrates which stimulate responses which recognise the whole organism.

Adjuvants

The term 'adjuvant' as used herein means an entity capable of augmenting or participating in the influencing of an immune response. An adjuvant is any substance or mixture of substances that assists, increases, downregulates, modifies or diversifies the immune response to an antigen.

The composition and/or pharmaceutical composition according to the present invention may comprise one or more adjuvants which enhance the effectiveness of the composition and/or pharmaceutical compositions. Examples of additional adjuvants which, may be effective include but are not limited to: aluminium hydroxide, aluminium phosphate, aluminum potassium sulphate (alum), beryllium sulphate, silica, kaolin, carbon, water-in-oil emulsions, oil-in-water emulsions, muramyl dipeptide, bacterial endotoxin, lipid X, *Corynebacterium parvum* (*Propionobacterium acnes*), *Bordetella pertussis, Mycobacterium vaccae*, polyribonucleotides, sodium alginate, lanolin, lysolecithin, vitamin A, interleukins such as interleukin 2 and interleukin-12, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.). Only aluminium hydroxide is approved for human use. Some of the other adjuvants, such as *M. vaccae* for example, have been approved for clinical trials.

Suitably, the adjuvant may be a whole cell of a bacterium from a genus of aerobic organisms in the order Actinomycetales.

In the art, it is known that DNA vaccines, which are essentially DNA sequences attached to gold particles and which are fired into the skin by a helium gun, are efficient vaccine delivery systems. Unlike conventional vaccines, these DNA vaccines do not require a traditional adjuvant component. In accordance with a further aspect of the present invention, the composition as defined herein may suitably be used in conjunction with such DNA vaccines to augment or participate in the influencing of an immune response.

Pharmaceutical Compositions

The present invention also provides a pharmaceutical composition comprising a therapeutically effective amount of a whole cell of a bacterium from a genus of aerobic organisms in the order of Actinomycetales and optionally a pharmaceutically acceptable carrier, diluent or excipients (including combinations thereof).

The pharmaceutical composition may comprise two components—a first component comprising an antigen and a second component comprising an adjuvant thereof. The first and second component may be delivered sequentially, simultaneously or together, and even by different administration routes.

Suitably, the antigen may even be engendered within the host tissues as part of a disease process. Thus, antigen may originate from a bacterial, host or parasitic invasion, or may be a substance released from the tissues such as a stress protein, equivalent to the heat-shock proteins of bacteria or a tumour antigen.

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a mini-pump or by a mucosal route, for example, as a nasal spray or aerosol for inhalation or ingestible solution, or parenterally in which the composition is formulated by an injectable form, for delivery, by, for example, an intravenous, intramuscular, intradermal or subcutaneous route. Alternatively, the formulation may be designed to be delivered by both routes.

Preferably in the present invention the formulation is of injectable form. More preferably the formulation is intradermally injected.

Preferably in the present invention the formulation is an orally acceptable composition.

Where the agent is to be delivered mucosally through the gastrointestinal mucosa, it should be able to remain stable during transit through the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly, intradermally or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner, or the compositions may be administered by incorporation into the food and/or feed of the subject.

Pharmaceutical Combinations

The agent of the present invention may be administered with one or more other pharmaceutically active substances. By way of example, the present invention covers the simultaneous, or sequential treatments with a composition and/or pharmaceutical composition according to the present invention, and one or more steroids, analgesics, antivirals, interleukins such as IL-2, or other pharmaceutically active substance(s).

In one embodiment the composition of the present invention may be administered with one or more pharmaceutically active substances which are typically used in the treatment of Type II diabetes. By way of example only such pharmaceutically active substances may include sulfonylureas, biguanides (e.g. metformin), thiazolidinediones, α-glucosidase inhibitors (e.g. acarbose and/or miglitol), meglitinides (e.g. nateglinide, repaglinide and/or their analogues), exenatide, and/or pramlintide.

For the avoidance of doubt, the one or more pharmaceutically active substances may be administered via the same or a different administration route as the composition as used in the present invention.

It will be understood that these regimes include the administration of the substances sequentially, simultaneously or together.

Immune Enhancer

The term "immune enhancer" as used herein means one or more bacteria either isolated or in culture which when administered to a subject benefit the health of that subject. Preferably, this benefit is achieved by the modification of the cellular immune response of the subject.

In accordance with the present invention, immune enhancers may be used for the treatment and/or prevention of Type II diabetes and/or obesity.

The immune enhancers may be administered by consumption in specially designed food or in animal feeds, for example animal feeds supplemented with the bacteria of the present invention.

The immune enhancers may also be administered by other routes—such as direct injection.

Preferably, the bacteria are killed so as to avoid the difficulties of maintaining live products and/or to expose immunologically active substances often hidden in live bacteria.

Identifying a Bacterium that can be Used to Treat Type II Diabetes

In another aspect, the present invention relates to a method for identifying one or more whole cells of bacteria from a genus of aerobic organisms in the order Actinomycetales that can treat and/or prevent Type II diabetes comprising the steps of: (a) administering a first group of test animals with an immunostimulant; (b) administering a second group of test animals with an immunostimulant mixed with a bacterium from a genera of aerobic organisms in the order Actinomycetales; (c) measuring the number or occurrences of and/or severity of Type II diabetes in each of the test animals (such as fasting blood glucose levels and/or glucose levels 2 hrs after glucose overdose); and (d) comparing the results in each of the groups of test animals, wherein, a lower occurrence of and/or severity of Type II diabetes from the immunostimulant mixed with a bacterium in comparison to the immunostimulant alone (e.g. a lower fasting blood glucose level) is indicative of a bacterium suitable for use in accordance with the present invention.

As used herein, the term "test animal" refers to any animal that elicits a cellular immune response to the immunostimulant. Preferably, the test animal(s) is a mammal. Preferably, the bacterium modifies the T helper cell response. Suitably, the bacterium may modify the T helper cell response by increasing the Th1 response and down-regulating the Th2 response.

Preferably, the immunostimulant will induce/enhance a known Th1 and Th2 response. For example, with the immunostimulant BCG the reaction to Tuberculin is usually largest at 24 h when it is an indicator of the Th1 response; the reaction at 48 h is usually less and includes a Th1 contribution. It is known that BCG predominantly stimulates a Th1 response in a naïve animal.

By use of such immunostimulants it may be possible to determine the Th1/Th2 response of a test bacterium and, thus, it may be possible to identify one or more bacteria which have a desired Th1/Th2 response to treat and/or prevent a particular disease and/or disorder.

Preferably, the cellular immune response is measured using the tuberculin skin test. In mice, the tuberculin skin test is preferably carried out on the foot pad. In a predominant Th1 reaction the positive foot pad immune response is maximal at 24 hours and diminishes at 48 hours. However, as the Th2 reactivity increases then the 48 hour positive foot pad immune response increases and can even exceed the foot pad immune response at 24 hour.

Vaccination with an immunostimulant—such as BCG—induces a response to skin-testing with tuberculin (a soluble preparation of *Tubercle bacilli*), when tested later. The local reaction is measured at various intervals, for example, 24 hours, 48 hours and 72 hours after injection of tuberculin. Briefly, an immunostimulant (e.g. BCG) is used that induces a positive immune response to tuberculin. In the test animal, the tuberculin skin test is preferably carried out on the foot pad. In a predominant Th1 reaction the positive foot pad immune response is usually maximal at 24 hours and diminishes at 48 hours. However, as the Th2 reactivity increases then the 48 hour positive foot pad immune response increases and can even exceed the foot pad immune response at 24 hour. Thus, the assay can be used to assess whether or not the introduction of an immune modulator composition according to the present invention modulates the cellular immune response.

Preferably, the immunostimulant is BCG.

FIGURES

Figure 2:
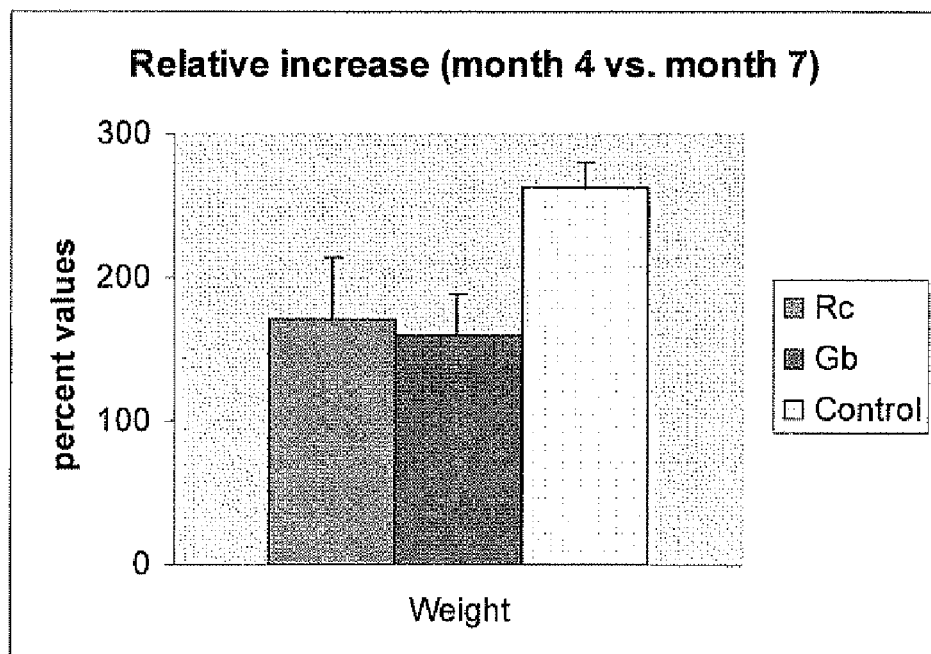

FIG. 1 shows a graph which depicts the relative increase in Glycaemia in eSMT rats at 7 months (i.e. 3 months post injection) compared with the eSMT rats at four months (i.e. immediately prior to injection). (Gb) refers to the group injected with *Gordonia bronchialis*, (Rc) refers to the group injected with *Rhodococcus coprophilus*; and FIG. 2 shows a graph which depicts the relative increase in weight in eSMT rats at 7 months (i.e. 3 months post injection) compared with the eSMT rats at four months (i.e. immediately prior to injection). (Gb) refers to the group injected with *Gordonia bronchialis*, (Rc) refers to the group injected with *Rhodococcus coprophilus*.

Figure 3:
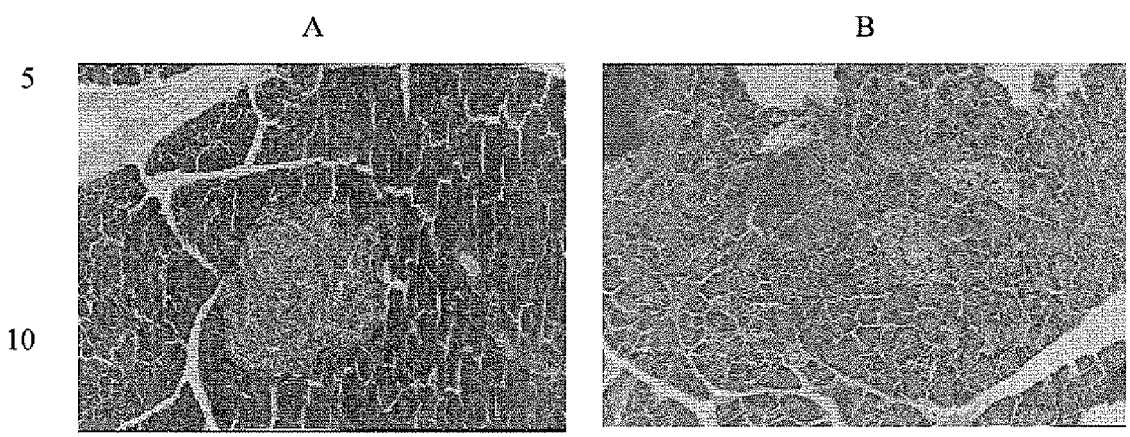

FIG. 3 shows Langerhans islets in diabetic rats. A shows a: Large islet (Haematoxilin & Eosin) 100× whilst B shows a Small islet (Haematoxilin & Eosin) 200×.

The invention will now be further described by way of Examples, which are meant to serve to assist one of ordinary skill in the art in carrying out the invention and are not intended in any way to limit the scope of the invention.

EXAMPLES

Example 1

Determination of the effects of administrating whole cells of *Gordonia bronchialis* (Gb) and *Rhodococcus coprophilus* (Rc) on the weight, fasting blood glucose levels and post glucose overdose blood glucose levels of diabetic rats.

Studies were carried out in a rat model of spontaneous Type II diabetes (eSMT rats—Rat Newsletter 1991; 25: 28-29; Supplement IV of the international Survey on the Supply, Quality and Use of Laboratory Animals, Carshalton, Surrey, UK November 1964 and Tarrés et al., The eSMT rat: a murine model of type 2 diabetes, proceedings of the international joint meeting twelfth general assembly and conference and seventh FELASA symposium, 26-28 May 1999) to resemble what happens in humans.

Three groups of 4-month aged rats were bled by tail vein puncture at fast and 120 min after an oral glucose overload for assessment of glucose levels, and also weighed (first evaluation). Glucose levels were measured by a glucose-oxidase enzymatic method using a commercial kit (Wiener Laboratories, Argentina).

Following that, groups were injected into the scruff of the neck with saline, 1 μg/0.1 ml *Rhodococcus coprophilus* in borate buffered saline or 1 g/0.1 ml *Gordonia bronchialis* in borate buffered saline, with a second identical administration three weeks later.

Three months later, the three groups of rats were bled at fast and 120 min after an oral glucose overload for assessment of glucose levels, and also weighed (first evaluation).

Results

The Study was Carried Out in a Rat Model of Spontaneous Type II Diabetes.

Table 1 shows the glucose levels at fast (G0) and 120 minutes after an oral glucose overload (G120), and weight of male eSMT (diabetic) rats at 4 months (pre-treatment) and at seven months.

Data are means±SD

TABLE 1

| GROUPS | Age: 4 mo. (pre treatment) | | | Age: 7 mo. (3 months post injection) | | |
|---|---|---|---|---|---|---|
| | G0 (mg/dl) | G120 (mg/dl) | Weight (g) | G0 (mg/dl) | G120 (mg/dl) | Weight (g) |
| Rc | 73 ± 11 | 108 ± 46 | 151 ± 20 | 118 ± 31 | 170 ± 45 | 259 ± 54 |
| Gb | 69 ± 9 | 87 ± 19 | 158 ± 14 | 94 ± 19 | 122 ± 26 | 249 ± 37 |
| CONTROL | 68 ± 5 | 80 ± 4 | 118 ± 4 | 175 ± 8 | 231 ± 44 | 311 ± 25 |
| P value | | | <0.025 | <0.005 | | <0.02 |

Table 2 shows the relative increaese when comparing 4-month vs. 7-month results

| | Glycaemia | | |
|---|---|---|---|
| Groups | Time 0 | Time 120 min | Weight |
| Rc | 163.2 ± 43.4 | 166.7 ± 43.7 | 171.5 ± 23.3 |
| Gb | 137.2 ± 28.6 | 146.7 ± 54 | 158.7 ± 28.8 |
| Control | 257.3 ± 17.9 | 290.7 ± 69 | 263 ± 13 |
| P value | 0.004 | 0.02 | 0.001 |

Example 2

Animals 24 male beta rats. Beta rats (and 2 other sub-lines: eSS and eSMT) are used as a model for non-insulin dependent human diabetes (see Tarrés et al., The eSS rat, American Journal of Pathology, September 1992, Vol. 141, No. 3 and Calderari et al., Rat News Letter, No. 25, July 1991, p 28-29; Olguín et al. Diabetes, Nutrition & Metabolism Clinical and Experimental 11: 314-319, 1998). Rats are available from Dr Maria Tarrés, Silvana Montenegro, Maria del Carmen Gayol and Dr Stella Maris Martínez (Cátedra de Biologia, Facultad de ciencias Médcas, UNR Santa Fe 3100. 2000 Rosario, Argentina)

Test Reagents

Heat-killed whole cells of *G. bronchialis* 100 μg/0.1 ml in borate buffered saline Heat-killed whole cells of *T. inchonensis* 100 μg/0.1 ml n borate buffered saline Saline placebo Protocol Aged 4 months the animals all had their resting and 120 minutes (post-glucose challenge) blood glucose levels measured.

All animals were weighed.

With this data, animals were randomised so that 12 rats remained as controls, 6 rats received 3 prophylactic doses of *G. bronchialis* (Gb) and 6 rats received 3 prophylactic doses of *T. inchonensis* (Ti).

The prophylactic doses were given when the rats were 4, 5 and 6 months old

At 7 months of age, rats were weighed and their fasting and post-glucose challenge glucose levels measured again.

On the basis of the weights and glucose levels, 6 of the control animals were randomised to receive treatment injections of *G. bronchialis*. These were given when the rats were 7, 8 and 9 months old.

At 1 year, animals were weighed and their resting and post-glucose challenge blood glucose levels were measured again.

Microscopy studies of the rats' pancreas were conducted in pancreas at 360 days and the number of large and small islets of Langerhans per microscopic field (at least 3 fields/pancreas), were counted at 100× according to a described method (Martínez S M, Tarrés M C, Picena J C, Montenegro S M, Gagliardino J J, Gómez Dumm C L, D'Ottavio A E, Naves A, Rabasa S L. eSS rat, an animal model for the study of spontaneous non-insulin-dependent diabetes. En: Lessons from Animal Diabetes IV. E Shafrir, Ed. Smith-Gordon, London, 75-90, 1993; Martínez S M, Tarrés M C, Robledo H A, Liborio M M, Picena J C, Rabasa S L. Modelo murino de la diabetes clínicamente benigna de los jóvenes (MODY). *Medicina (Buenos Aires)* 44: 145-152, 1984; and Martínez S M, Tarrés M C, Montenegro S M, Milo R, Picena J C, Figueroa N, Rabasa S L. Spontaneous diabetes in eSS rats. *Acta diabetol lat* 25: 303-313, 1988).

An islet with a diameter oscillating between the diameter of 1 to less than 3 pancreatic acini's was defined as small, whereas an islet showing a diameter equal or greater than 3 pancreatic acini's was regarded as large. For calculation of the insular area, small and large islets were given values 1 and 3, respectively. By using a calibrated (Shimadzu®) linear scale placed in the eyepiece of a microscope (400×), small islets were found to have a maximum diameter of 35 lines (118.3 μm) with large islets having a maximum diameter of 36 lines (121.7 μm). In other words, 120 μm established the limit between small and large islets.

As depicted in FIG. 3, small islets had a <3 acini diameter (<120 μm), whereas large had a =>3 acini's (>120 μm).

Histological specimens under analysis only comprised pancreatic parenchyma.

Results

Table 3 shows the glucose levels at fast (G0) and 120 minutes after an oral glucose overload (G120), weight (w), triglycerides (TG) and Cholesterol (Col) of male beta (diabetic) rats at 4, 6, 8 and 12 months. Group A was inoculated with *G. bronchialis* (Gb) at 120, 150 and 180 days; Group B was inoculated with *T. inchonensis* (Ti) at 120, 150 and 180 days; Group C was inoculated with *G. bronchialis* (Gb) at 7, 8 and 9 months and Group D is the control group. Data are means±SD

TABLE 3

| | AGE | | | | | | | | | |
|---|---|---|---|---|---|---|---|---|---|---|
| | 120 days | | | | | 180 days | | | | |
| Group | W | G0 | G120 | TG | Col | W | G0 | G120 | TG | Col |
| a) | 289 ± 20 | 113 ± 13 | 126 ± 7 | 217 ± 67 | 79 ± 13 | 328 ± 17 | 143 ± 21 | 132 ± 18 | 151 ± 40 | 80 ± 9 |
| b) | 286 ± 27 | 112 ± 12 | 114 ± 14 | 196 ± 60 | 84 ± 12 | 337 ± 19 | 147 ± 9 | 130 ± 15 | 126 ± 33 | 76 ± 10 |
| c) | 301 ± 18 | 111 ± 21 | 120 ± 12 | 169 ± 38 | 81 ± 13 | 353 ± 15 | 142 ± 29 | 134 ± 14 | 206 ± 37 | 83 ± 15 |
| d) | 294 ± 22 | 114 ± 20 | 125 ± 18 | 214 ± 49 | 90 ± 17 | 370 ± 24 | 145 ± 32 | 148 ± 26 | 220 ± 21 | 90 ± 14 |
| ANOVA (p) | ns | ns | ns | ns | ns | <.01 | ns | ns | <.001 | <.001 |
| TUCKEY(p) | | | | | | | | | | |
| a) vs b) | | | | | | >.05 | | | >.05 | >.05 |
| a) vs c) | | | | | | >.05 | | | <.05 | <.001 |
| a) vs d) | | | | | | <.01 | | | <.01 | >.05 |
| b) vs c) | | | | | | >.05 | | | <.01 | <.001 |
| b) vs d) | | | | | | <.05 | | | <.001 | >.05 |
| c) vs d) | | | | | | >.05 | | | >.05 | <.001 |
| | 270 days | | | | | 360 days | | | | |
| Group | W | G0 | G120 | TG | Col | W | G0 | G120 | TG | Col |
| a) | 433 ± 26 | 149 ± 23 | 148 ± 28 | 220 ± 62 | 94 ± 14 | 427 ± 56 | 151 ± 25 | 164 ± 38 | 290 ± 84 | 108 ± 18 |
| b) | 371 ± 25 | 137 ± 13 | 127 ± 25 | 170 ± 37 | 96 ± 7.5 | 405 ± 30 | 126 ± 17 | 124 ± 36 | 214 ± 51 | 115 ± 7 |
| c) | 407 ± 16 | 130 ± 21 | 141 ± 14 | 230 ± 61 | 95 ± 14 | 452 ± 18 | 119 ± 14 | 148 ± 18 | 304 ± 86 | 107 ± 15 |
| d) | 470 ± 40 | 193 ± 37 | 269 ± 59 | 279 ± 33 | 104 ± 21 | 487 ± 45 | 180 ± 42 | 281 ± 53 | 301 ± 76 | 93 ± 12 |
| ANOVA (p) | <.001 | <.01 | <.001 | <.05 | ns | <.05 | <.01 | <.001 | ns | ns |
| TUCKEY(p) | | | | | | | | | | |
| a) vs b) | <.01 | >.05 | >.05 | >.05 | | >.05 | >.05 | >.05 | | |
| a) vs c) | >.05 | >.05 | >.05 | >.05 | | >.05 | >.05 | >.05 | | |
| a) vs d) | >.05 | <.05 | <.001 | >.05 | | >.05 | >.05 | <.001 | | |
| b) vs c) | >.05 | >.05 | >.05 | >.05 | | >.05 | >.05 | >.05 | | |
| b) vs d) | <.001 | <.01 | <.001 | <.01 | | <.01 | <.05 | <.001 | | |
| c) vs d) | <.01 | <.01 | <.001 | >.05 | | >.05 | <.01 | <.001 | | |

In line with laboratory studies, animals given Gb or Ti had a trend to show larger islets compared with the control group in the microscopy results.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A method for treating or preventing Type II diabetes and/or a method of treating obesity in a subject comprising administering an effective amount of a composition comprising whole cells of bacteria from a genus of aerobic organisms in the order of Actinomycetales, to said subject with Type II diabetes or a predisposition for Type II diabetes selected from the group consisting of: high cholesterol, obesity and a genetic predisposition to Type II diabetes, wherein said bacteria are selected from one or more of the following genera: *Gordonia, Rhodococcus, Tskukamurella, Nocardia, Dietzia* and *Mycobacterium*.

2. The method according to claim 1 wherein said bacteria is a mycolic acid containing bacteria.

3. The method according to claim 1 wherein said bacteria are selected from one or more of the following species: *Gordonia bronchialis, Rhodococcus coprophilus, Tsukamurella inchonensis, Tsukamurella paurometabola, G. amarae, G. sputi, G. terrae, Nocardia asteroides, N. brasiliensis, Tsukamurella paurometabola, Rhodococcus ruber, Rhodococcus rhodnii, R. opacus, R. erythopolis, Dietzia maxis, Mycobacterium vaccae* and *M. obuense*.

4. The method according to claim 1 wherein said bacteria are from the genus *Gordonia*.

5. The method according to claim 4 wherein said bacteria are of the species *Gordonia bronchialis*.

6. The method according to claim 1 wherein said bacteria are from the genus *Rhodococcus*.

7. The method according to claim 6 wherein said bacteria are of the species *Rhodococcus coprophilus*.

8. The method according to claim 1 wherein said bacteria are from the genus *Tsukamurella*.

9. The method according to claim 8 wherein said bacteria are of the species *Tsukamurella inchonensis*.

10. The method according to claim 1 wherein said bacteria are killed.

11. A method for treating or preventing one or more of insulin resistance when associated with Type II diabetes, insulin deficiency when associated with Type II diabetes and hyperglycaemia when associated with Type II diabetes and metabolic syndrome when associated with Type II diabetes in a subject comprising administering an effective amount of a composition comprising whole cells of bacteria from a genus of aerobic organisms in the order of Actinomycetales, to said subject with one or more of insulin resistance when associated with Type II diabetes, insulin deficiency when associated with Type II diabetes and hyperglycaemia when associated with Type II diabetes and metabolic syndrome when associated with Type II diabetes or a predisposition therefor selected from the group consisting of: high cholesterol, obesity and a genetic disposition to Type II diabetes, wherein said bacteria are selected from one or more of the following genera: *Gordonia, Rhodococcus, Tsukamurella, Nocardia, Dietzia* and *Mycobacterium*.

* * * * *